United States Patent [19]

Lindahl et al.

[11] Patent Number: 4,835,307

[45] Date of Patent: May 30, 1989

[54] METHOD AND APPARATUS FOR CONTROLLING THE MANUFACTURE OF TEREPHTHALIC ACID TO CONTROL THE LEVEL AND VARIABILITY OF THE CONTAMINANT CONTENT AND THE OPTICAL DENSITY

[75] Inventors: Harold A. Lindahl, Riverside; Kenneth J. Abrams, Naperville; Leonard E. Stark, Naperville; Martin A. Zeitlin, Naperville, all of Ill.

[73] Assignee: Amoco Corporation, Chicago, Ill.

[21] Appl. No.: 681,227

[22] Filed: Dec. 13, 1984

[51] Int. Cl.$^4$ .............................................. C07C 51/265
[52] U.S. Cl. .................... 562/413; 562/414; 562/416
[58] Field of Search .................. 562/413, 414, 416

[56] References Cited

U.S. PATENT DOCUMENTS 4,197,412  4/1980  Kimura et al. .................. 562/416
4,314,073  2/1982  Crooks ............................ 562/416

FOREIGN PATENT DOCUMENTS 160330  12/1979  Japan.

OTHER PUBLICATIONS

Perry, R. H., Ed., Chemical Engineer's Handbook, Fifth Ed., McGraw-Hill Book Co., New York, 1973, pp. 22-104-22-108.

Primary Examiner—Michael L. Shippen
Attorney, Agent, or Firm—James R. Henes; William H. Magidson; Ralph C. Medhurst

[57] ABSTRACT

The method and apparatus for manufacturing terephthalic acid (TA) are capable of producing TA having a closely controlled, desired amount of contaminant, 4-carboxy-benazldehyde (4-CBA), therein and/or a closely controlled optical density. In the method, a feed of para-xylene or similar feedstock mixed with catalyst components and solvent system is fed to a reactor stage comprising one or more reactors with oxygen for carrying out an exothermic oxidation reaction in the reactor stage, and an output slurry from the reactor stage is fed with oxygen to a first crystallizer of a crystallizing stage. The method comprises the steps of: determining empirical relationships between (1) the desired level of contaminant in the TA output product from the crystallizing stage and the oxygen uptake in the first crystallizer and (2) the oxygen uptake in the first crystallizer and the $CO_2$ in the vent gas from the reactor stage; monitoring the $CO_2$ in the vent gas from the reactor stage; and, adjusting operating variables of the reactor stage within minimum and maximum constraints thereof to adjust the reactor vent $CO_2$ to a desired level.

Also, the method includes the steps of: determining empirically a mathematical relationship between the oxygen in the vent gas from the reactor stage and the opticals or optical density of the TA output product; monitoring the oxygen in the vent gases; and, adjusting the air intake to the reactor stage until the oxygen in the reactor vent gas is at a desired level to provide TA output product with a desired optical density.

The apparatus includes one or more reactors, one or more crystallizers, and control devices for carrying out the various steps of the method.

16 Claims, 3 Drawing Sheets

METHOD AND APPARATUS FOR CONTROLLING THE MANUFACTURE OF TEREPHTHALIC ACID TO CONTROL THE LEVEL AND VARIABILITY OF THE CONTAMINANT CONTENT AND THE OPTICAL DENSITY

BACKGROUND OF THE INVENTION

1. Field of the Invention

The present invention relates to a method and apparatus for the manufacture of highly pure terephthalic acid with closely controlled output quality with respect to amount and levels of contaminant content, namely 4-carboxy-benzaldehyde (4-CBA) and optical density which affects coloration of the terephthalic acid (TA).

2. Description of the Prior Art

Heretofore it has been known to manufacture TA by first preparing a feed including a p-dialkylbenzene such as para-xylene mixed with a catalyst such as cobalt and/or manganese and a bromine from a bromine source plus a solvent system. Then the feed preparation is fed to one or more reactors with air and a controlled exothermic oxidation reaction takes place in the reactor(s) to form TA.

Then a TA slurry from the reactor(s) is supplied to a first crystallizer of a crystallization stage which may include one or more crystallizers. Again, air is supplied to the first crystallizer along with the TA slurry and some further oxidation occurs. The TA is then supplied to a product recovery stage where it is separated and dried. Dry TA produced is then sent to storage.

In such a method for the manufacture of TA, it has been proposed to provide certain controls to enhance the purity or quality of the TA output product produced.

In this respect, reference is made to Japanese Pat. No. 160330/79 for: METHOD FOR THE MANUFACTURE OF HIGHLY PURE TEREPHTHALIC ACID WITH CONSTANT QUALITY issued to the Kuraray Yuka Co., Ltd.

In this Japanese patent, it is taught to control the reaction temperature, the supply rate of the TA p-dialkylbenzene, the catalyst concentration, the supply rate of air and/or water content in the acetic acid solvent supplied to the feed to maintain constant the concentration of $H_2$ or $CH_4$ in the exhaust gas or the generation of $H_2$ or $CH_4$ and the ratio of the gaseous carbon components generated and the supply rate of the p-dialkylbenzene to the TA production process.

Stated otherwise, the variability of crude optical properties and 4-CBA are controlled by keeping both the $H_2$ (or $CH_4$) and $CO_x$ production rates constant in a reactor.

Secondly, the $H_2$ and $CO_X$ production rates are maintained constant by manipulating one or more of the following variables or parameters: reaction temperature, p-xylene feed rate, air feed rate, feed mix composition and solvent water content.

Thirdly the method disclosed in the Japanese patent teaches that variability for both 4-CBA and optical density were reduced from 6 to 13% to 2 to 3% of the mean value.

As will be described in greater detail hereinafter, the method of the present invention and the apparatus implementing same differ from the teachings of the Japanese patent by providing for the continous measurement of indicator variables for both controlling optical density and 4-CBA content in the TA output product as opposed to utilizing discrete gas samples to monitor the optical density or opticals of the output product.

Secondly, the method and apparatus of the present invention allow for control of the level of the optical density (opticals) and the 4-CBA content in addition to reducing variability as opposed to the teachings of the Japanese patent which only teach reducing variability.

The method of the present invention is carried out on the basis of the recognition of the relationship between product 4-CBA content levels, colors or opticals of the TA product, and reactor vent oxygen concentration. In this respect, the following correlation was noted:

$$OD_{340nm} \alpha \frac{[4 - CBA \text{ content}]^{0.5}}{[\text{reactor vent } O_2]^{0.5}}$$

With this relationship, the method of the present invention is utilized to control variability and level of crude TA opticals indirectly by controlling the reactor 4-CBA production and the reactor vent oxygen concentration. Typically, reactor and product 4-CBA levels are continuously monitored in the process by using two indicator variables, namely the reactor carbon dioxide production and the secondary oxidation oxygen uptake in the first crystallizer for controlling 4-CBA content. Then, in addition, reactor vent oxygen concentration is monitored for controlling optical density of the TA output product.

SUMMARY OF THE INVENTION

According to the present invention there is provided a method for manufacturing terephathalic acid (TA) having a closely controlled, desired amount of contaminant, 4-carboxy-benzaldehyde (4-CBA), therein and in which method a feed of para-xylene or similar feedstock mixed with catalysts and a solvent system is fed to a reactor stage comprising one or more reactors with oxygen for carrying out an exothermic oxidation reaction in the reactor stage, and an output slurry from the reactor stage is fed with oxygen to a first crystallizer of a crystallizing stage, said method comprising the steps of: determining empirical relationships between (1) the desired level of contaminant in the TA output product from the crystallizing stage and the oxygen uptake in the first crystallizer and (2) the oxygen uptake in the first crystallizer and the $CO_2$ in the vent gas from the reactor stage; monitoring the $CO_2$ in the vent gas from the reactor stage; and, adjusting operating variables of the reactor stage within minimum and maximum constraints thereof to adjust the reactor vent $CO_2$ to a desired level.

Additionally, the method can include the steps of: once the desired $CO_2$ level is obtained, confirming that the oxygen uptake in the first crystallizer is the value it should be relative to the $CO_2$ in the reactor vent gas; if the oxygen uptake in the crystallizer is not the desired value, obtaining a new target value for the reactor vent $CO_2$ content from the empirically determined relationships; and, analyzing analytically the percentage of the contaminant in the dried TA output product to make certain it is within the desired range.

Further according to the invention, the method can include the steps of: determining empirically a mathematical relationship between the oxygen in the vent gas from the reactor stage and the opticals or optical density of the TA output product; monitoring the oxygen in the vent gases; and, adjusting the air intake to the reactor stage until the oxygen in the reactor vent gas is at a desired level to provide TA output product with a desired optical density.

Also, according to the invention there is provided an apparatus for manufacturing a terephthalic acid (TA) having a closely controlled, desired amount of contaminant, 4-carboxy-benzaldehyde (4-CBA), therein said apparatus comprising: a reactor stage including one or more reactors; means for feeding para-xylene or similar feedstock mixed with catalysts and solvent system to said reactor stage; means for feeding oxygen to said reactor stage so that an exothermic oxidation reaction can take place in the reactor stage; a first crystallizer; means for feeding an output slurry from the reactor stage to said first crystallizer; means for feeding oxygen to said crystallizer; control means coupled to said reactor stage and to said first crystallizer for utilizing empirically determined relationships between (1) the level of contaminant in the TA output product from the crystallizing stage and the oxygen uptake in the crystallizer and (2) the oxygen uptake in the first crystallizer and the $CO_2$ in the reactor vent gas; means coupled between said control means and said reactor stage for monitoring the $CO_2$ in the vent gas from the reactor stage; means including said control means for adjusting operating variables of the reactor stage within constraints thereof to adjust the reactor vent $CO_2$ to a desired level; means including said control means for confirming that the oxygen uptake in the first crystallizer is the value it should be relative to the $CO_2$ in the reactor vent gas to obtain a desired level of contaminant in the dried TA output product produced by the apparatus; and means for adjusting the desired level of $CO_2$ in the reactor vent gas if the oxygen uptake in the crystallizer is not at the desired value at a predetermined desired value of $CO_2$ in the reactor vent gas.

Still further according to the invention said control means of said apparatus is operable to utilize an empirically determined mathematical relationship between the oxygen in the vent gas from the reactor stage and the opticals or optical density of the TA output product for controlling the optical density of the TA output product; and said apparatus further includes means coupled between said reactor stage and said control means for monitoring the oxygen in the reactor vent gas; and means coupled between a reactor air intake line and said control means for adjusting the air intake to the reactor stage until the oxygen in the reactor vent gas is at a desired level to provide TA output product with a desired optical density.

DESCRIPTION OF THE PREFERRED EMBODIMENT

Figure 1:
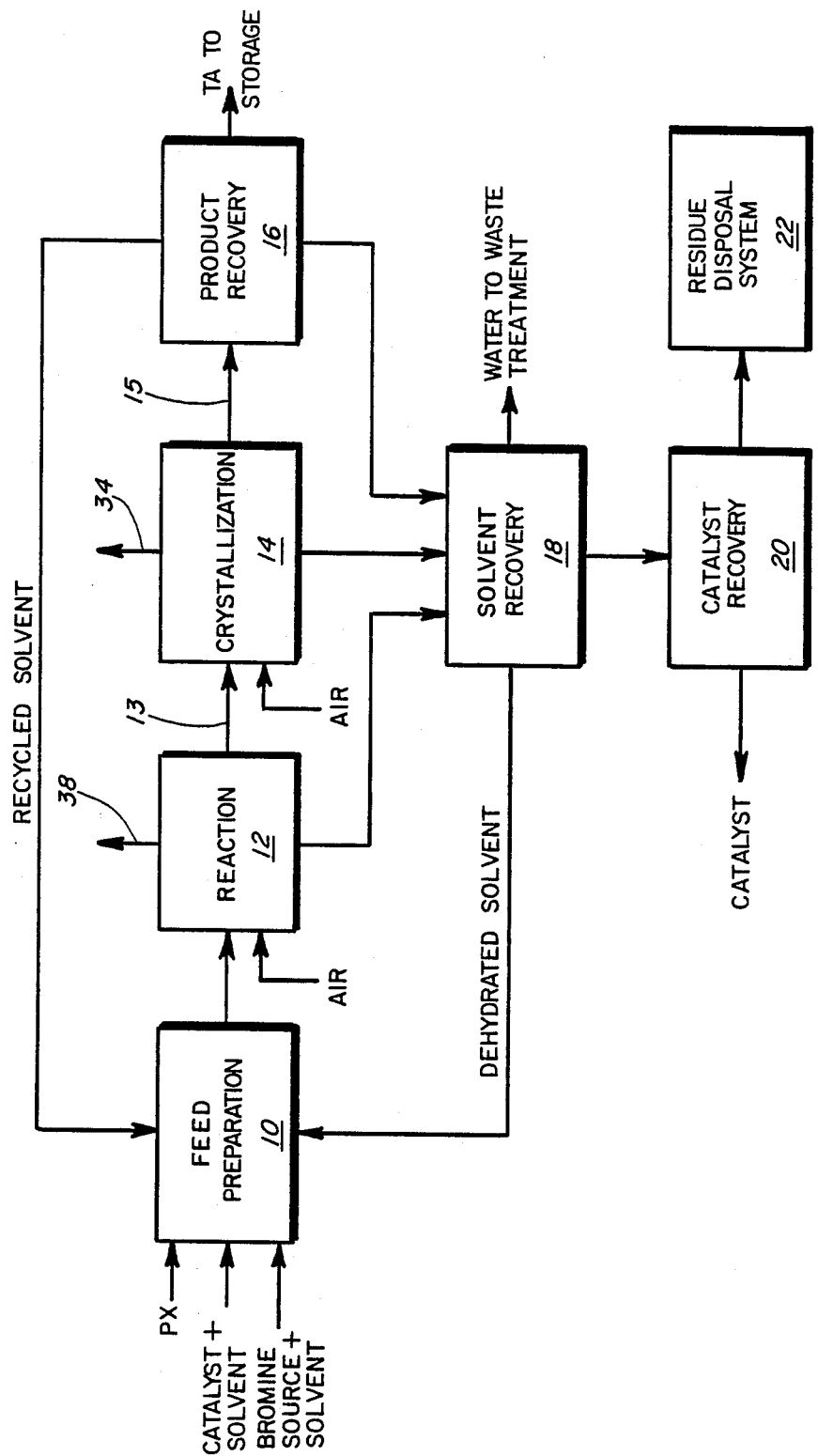
FIG. 1 is a process flow diagram of a process for manufacturing terephthalic acid utilizing the method of the present invention.

Referring now to the drawings in greater detail, there is illustrated in FIG. 1 a process flow diagram of a process for manufacturing terephthalic acid (TA).

The first stage of the process is a feed preparation stage 10 where the feed is prepared. Typically, in the feed preparation stage, solvent and catalyst are mixed with a p-dialkylbenzene, such as para-xylene (pX). More specifically, a metal catalyst such as cobalt and/or manganese salts in a solvent solution are mixed with the pX. Also bromine from a bromine source is fed to the feed preparation stage 10 with a solvent such as acetic acid and mixed with the other components of the feed.

The para-xylene (pX), the catalyst such as cobalt and/or manganese, the bromine, and the solvent system, are mixed in the feed preparation stage 10 and then fed to a reaction stage 12 which is also supplied with air and which may comprise one or more reactor sections or vessels. In the reaction stage 12 an exothermic air oxidation reaction occurs to form TA.

The TA slurry from the reaction stage 10 is supplied via an input line 13 and with air to a crystallization stage 14 which may comprise one or more crystallizers.

In the crystallization stage 14, impurities are oxidized.

As will be described in greater detail hereinafter, the reactions in the reaction stage 12 and in the crystallization stage 14 are controlled in order to control the amount of the primary impurity, 4-carboxy-benzaldehyde (4-CBA), in the TA produced and to control the optical density of the TA product.

The optical density of the TA product determines the "opticals", i.e., how much coloring agent or optical brightener needs to be added to the polyester made from the terephthalic acid (TA).

The amount of 4-CBA in the TA product affects and/or controls the length of the polyester polymer produced when the TA product reacts with a glycol solution. It also affects and/or controls the polymer breakdown and the strength of the polymer.

The amount of 4-CBA contaminant is controlled so that the TA product will have a high level of uniformity with respect to the amount of 4-CBA contaminant. Also, the range of variance from a target level of 4-CBA in the TA product is tightly controlled to obtain better operating efficiencies resulting in cost savings and overall better economics.

The control of the reactions in the reaction stage 12 and in the crystallization stage 14 according to the teachings of the present invention will be described in greater detail hereinafter in connection with the description of FIG. 2.

The product output from the crystallization stage 14 is supplied via a line 15 to a product recovery stage 16 where, by means of a filter and/or centrifuge, physical separation of the solid TA from liquid is obtained.

Then some of the solvent is recycled back to the feed preparation stage 10 and other solvent with catalyst is supplied to a solvent recovery stage 18.

It will be noted that solvent is also recovered from the reaction stage 12 and from the crystallization stage 14 and supplied to the solvent recovery stage 18.

The solvent recovery stage 18 is typically a water distillation stage where water is removed and supplied to a waste treatment facility, while recovered solvent, e.g., acetic acid, is recycled back to the feed preparation stage 10.

The solid residue from the solvent recovery stage 18 is supplied to a catalyst recovery stage 20. Here a leaching process is employed for removing solid catalyst from the residue supplied to the catalyst recovery stage.

The remaining residue is then supplied to a residue disposal system 22.

Figure 2:
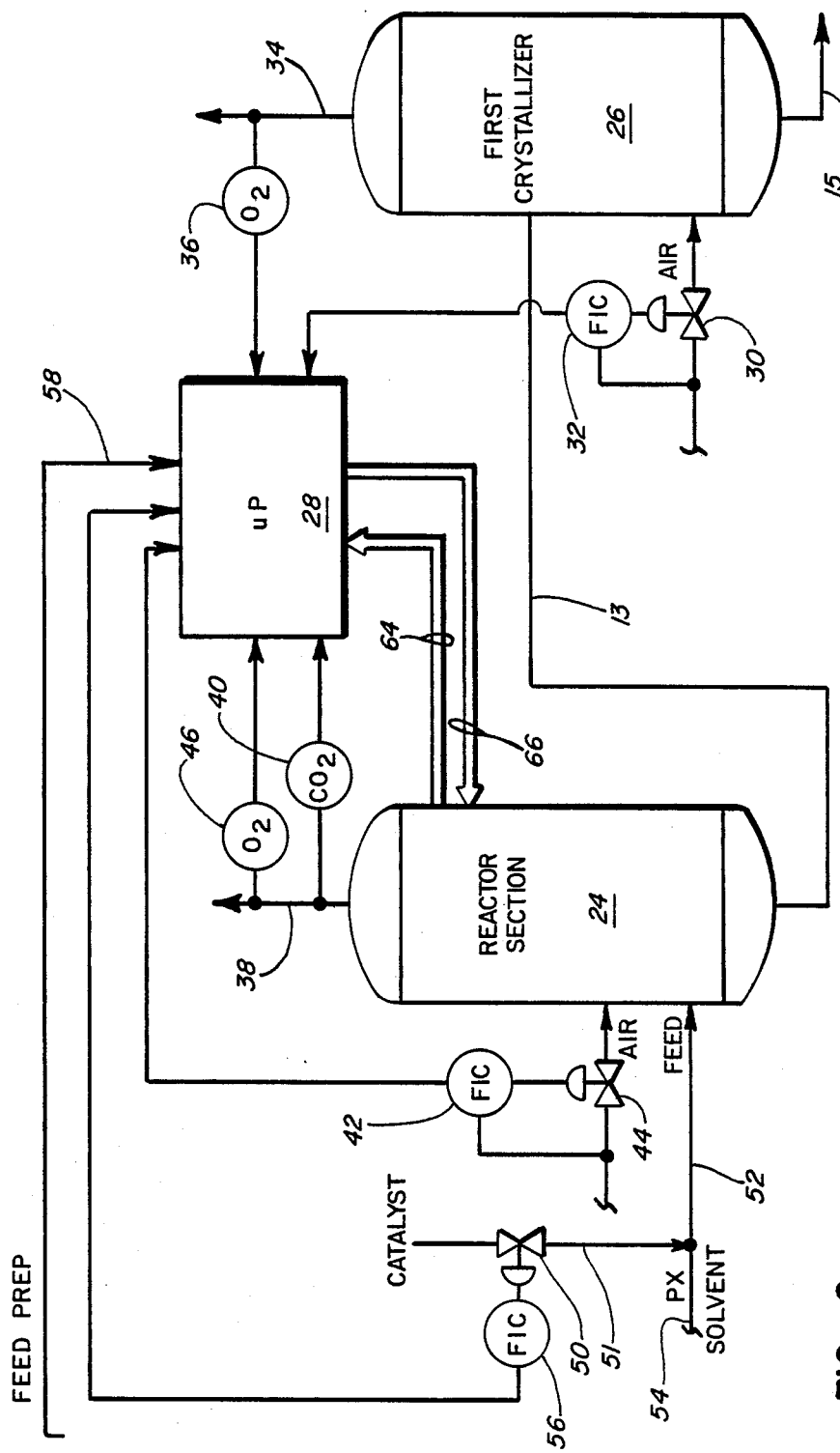
FIG. 2 is a block flow diagram of a reactor section in the reactor stage and of a first crystallizer in the crystallization stage shown in FIG. 1 and shows control valves, gas sensors and a microprocessor utilized in practicing the method of the present invention to achieve a very uniform quality level of terephthalic acid product.

In accordance with the teachings of the present invention and with reference to FIG. 2, the method of the present invention is utilized with one or more reactor vessels or sections 24 and at least one first crystallizer 26 for the manufacture of highly pure terephthalic acid (TA). According to the method, certain indicator variables or parameters are continuously measured once the process has reached a steady state condition and these indicator variables are utilized by a computer system 28 including a microprocessor for controlling both optical density (O.D. at 340 nm) and the level of contaminant (4-CBA).

In accordance with the teachings of the present invention, the 4-CBA concentration in a crude TA output product is controlled using the variables of measured reactor $CO_2$ production in the reactor section 24 and the secondary oxidation $O_2$ uptake in the first crystallizer 26.

The secondary oxygen uptake in the first crystallizer 26 is easily determined by subtracting the $O_2$ out from the $O_2$ into the first crystallizer 26. This is accomplished by sensing the air flowing through a controlled air intake valve 30. A flow sensor/valve controller 32 is coupled between the valve 30 and the computer system 28 for sensing and controlling the flow of air. Then this flow rate is compared with the vent oxygen concentration (between 1% and 26%) in a vent 34 from the first crystallizer 26 (as sensed by an oxygen sensor 36 coupled between the vent 34 and the computer system 28) to determine secondary oxygen uptake for controlling the 4-CBA concentration in the TA product.

From measured operating variables it has been determined that there is an empirical relationship between (1) the desired level of contaminant in the TA output product from the crystallizing stage and the oxygen uptake in the first crystallizer and (2) the oxygen uptake in the first crystallizer and the $CO_2$ in the vent gas from the reactor stage.

Accordingly, the computer system 28 first determines if the secondary oxygen uptake is at a desired value related to the $CO_2$ in the vent gas from the section 24.

If it is not at the desired level, the $CO_2$ in a vent 38 from the reactor section 24 is sensed (by a $CO_2$ sensor 40 coupled between the vent 38 and the computer system 28) to see if it is at the empirically predetermined level. The $CO_2$ is affected by the indicator values as well as by the air into the reactor stage 24 as controlled by an air flow sensor/valve controller 42 and valve 44 (in the air intake line to reactor section 24).

Since the air flow into the reactor section 24 had been previously set so that approximately 90% of the oxidation occurs in the reactor section 24 and so that a desired $O_2$ level in the vent gases is obtained for obtaining a desired optical density, the air flow into the reactor section 24 is not altered. Typically the air rate is adjusted so that the $O_2$ level in the vent gases is in the range of about 1% to about 12%, preferably about 1% to 7%.

Instead, to obtain the desired level of $CO_2$ in the vent 38, first the temperature is adjusted within a range (constraints) of between 350° F. to 500° F., and more specifically between 375° F. and 450° F.±10° F. An increase in temperature results in a reduction of 4-CBA and vice versa.

If the $CO_2$ is still not at the right level and a maximum or minimum temperature constraint has been reached, the water content in the reactor section 24 is adjusted within a range (constraints) of between 5% and 20% by weight.

Again, if a maximum or minimum water content constraint is reached and the $CO_2$ is still not at a target level, a third variable, namely weight percent of catalyst, is adjusted.

When the catalyst comprises soluble forms of cobalt, manganese and bromine: cobalt (calculated as elemental cobalt) can be present in the range of from about 0.1 to about 10.0 milligram atoms (mga) per gram mole of the alkyl aromatic; manganese (calculated as elemental manganese) can be present in a ratio of from about 0.1 to about 10.0 mga per mga of cobalt (calculated as elemental cobalt); and bromine (calculated as elemental bromine) can be present in a ratio of from about 0.2 to about 1.5 mga per mga of the total cobalt and manganese (both calculated as elemental metals).

Again, if the maximum or minimum constraints of these ranges are met and the $CO_2$ is still not at the desired level, the level of material in the reactor section 24 is altered. The range of level of material is between 50% and 90% by volume.

Although one should be able to establish the target reactor vent $CO_2$ to obtain a desired secondary $O_2$ uptake in the first crystallizer 26 by varying one or more of the variables of: temperature, water, catalyst, or level of material in the reactor, if it is still not obtained, one can expand the range of the constraints or recalibrate the relationship between reactor vent $CO_2$ and secondary $O_2$ uptake and then repeat the above steps.

Once the desired target $CO_2$ content in the reactor vent 38 and the corresponding $O_2$ uptake in the first crystallizer section 26 are met, the TA product quality is checked to see if it is where it should be with respect to the 4-CBA content thereof. In this respect, every four hours an analytical analysis of the dried "cake" of TA is made in a laboratory to determine the 4-CBA content and the 4-CBA content is fed back to the computer system 28.

If the TA product quality is not what it should be as previously empirically determined for the target $CO_2$ content in the reactor vent 38 relative to the target $O_2$ uptake in the first crystallizer section 26, one first changes the $O_2$ uptake target. Then one changes $CO_2$ target to get the new $O_2$ target. Next the relationship between the $CO_2$ in the vent 38 and the $O_2$ uptake in the first crystallizer section 26 is recalibrated by the computer system 28.

Meanwhile, vent oxygen concentration from the reactor section 24 is sensed by a oxygen sensor 46 coupled to vent 38 from the reaction section 24. An electrical signal related to the oxygen concentration is supplied by sensor 46 to the computer system 28. Then the oxygen concentration is controlled between 1% and 6% by adjusting sensor/controller 42 to control the level of oxygen input to control oxygen in the vent gas to control the opticals of, i.e., optical density of, the TA product independent of the 4-CBA concentration in the TA product.

Although the optical density is usually controllable independent of the 4-CBA concentration variables, after the reactor vent $O_2$ is set at the desired level, the reactor vent $CO_2$ is checked and the reactor variables adjusted if necessary to bring the reactor vent $CO_2$ back in line with the target $CO_2$.

From the foregoing description it will be apparent that the 4-CBA in a crude TA product output is controlled by maintaining a predetermined reactor vent $CO_2$ value related to a predetermined $O_2$ uptake value in the first crystallizer 26 constant.

Secondly, so-called opticals, namely color and optical density, of the crude TA output product are controlled using the reactor vent $O_2$ concentration as an independent variable.

Thirdly, the control is effected using the computer system 28.

As shown in FIG. 2, the amount of heavy metal catalyst such as cobalt and/or manganese in the feed is controlled by a valve 50 in a catalyst input line 51 coupled to a feed input line 52 which also receives pX and solvent from a line 54. The valve 50 is controlled by a sensor/controller 56 that is coupled to the computer system 28. The composition of the feed preparation in terms of pX, solvent, and bromine is supplied to the computer system 28 via an input line 58. The amount of air fed to the reactor section 24 through the valve 44 is sensed and controlled by the controller 42.

Also, sensors are provided for sensing reactor level, reactor temperature and the amount of water draw off. The values of these variables is supplied via input lines 64 to the computer system 28. Output control lines 66 are used to effect control of these variables in the operation of the reactor section 24.

The various parameters and variables of operation of the process illustrated in FIGS. 1 and 2 are adjustable in a manner which will be more fully described below. Optimum target values for the parameters can be calculated and utilized by the computer system 28.

The first crystallizer 26 oxygen uptake per mole of pX feed to reactor section 24 defines a performance index (PI) which is an indication of the 4-CBA content of the crude TA exiting the product recovery stage 16. Optimum values for the PI of the first crystallizer 26 are obtained by controlling the 4-CBA content in the reactor effluent.

The $CO_2$ generation per mole of pX feed in the reactor section 24 is the index of performance which indicates the amount of 4-CBA in the reactor effluent.

The PI determined for the reactor section 24 from a target $CO_2$ can be adjusted first by adjusting the temperature of the reactor section 24 to the minimum or maximum constraints thereof.

If the contraints of temperature are reached prior to obtaining a desired PI, the concentration of water in the reactor 24 is then adjusted to the maximum or minimum constraints placed thereon.

If the constraints of water concentration are reached prior to obtaining a desired PI, the concentration of catalyst within the reactor section 24 is adjusted to the minimum or maximum constraints placed thereon.

By interfacing of the first crystallizer 26 and reactor section 24 through a computer system 28, the process variables defined above can be manipulated and these variables can be sequenced through each of the reactors provided.

The first crystallizer 26 oxygen uptake per mole of pX feed to reactor section 24 can be determined by the following equation:

$$A = \frac{(7.48)(106.168)(B)[0.21-0.79C/(100-C-G)]}{379 \, DEF} \quad (1)$$

where:
- A = first crystallizer 26 oxygen uptake per mole of pX fed into reactor section 24 in units of moles of oxygen per mole of pX feed;
- B = air flow rate to the first crystallizer 26, in units of SCFM (Standard Cubic Feet per Minute);
- C = oxygen concentration in the vent from the first crystallizer 26 in units of mole percent;
- D = PX concentration (in weight fraction or decimal) in the reactor feed input stream;
- E = density of incoming reactor feed input stream in pounds per cubic foot;
- F = flow rate of the incoming reactor feed input stream in gpm (gallons per minute), and
- G = carbon dioxide concentration in the vent from the first crystallizer 26 in mole percent.

Further, the setpoint or desired value for the first crystallizer 26 oxygen uptake per mole of pX feed being fed into the reactor section 24 is determined using the following correlation:

$$A = B^N C^J D^L E^M \exp(K_1 - K_2/F) \quad (2)$$

where:
- A = first crystallizer 26 oxygen uptake per mole of pX feed fed into reactor section 24, in moles of oxygen per mole of feed;
- B = setpoint or desired value for the 4-CBA in weight percent;
- C = oxygen concentration in the vent 34 from the first crystallizer 26 in mole percent;
- D = concentration of cobalt in the reactor feed input stream in ppm allowing for the time delay between the reactor feed input stream and the first crystallizer;
- E = a throughput term obtained by multiplying together:
  1. the pX concentration (in weight fraction or decimal) in the reactor feed input stream allowing for the time delay between the reactor feed input stream and the first crystallizer;
  2. the density of the reactor feed input stream in pounds per cubic foot, and
  3. the flow rate of the reactor feed input stream in gpm, allowing for the time delay between the reactor feed input stream and the first crystallizer;
- F = the absolute temperature in the first crystallizer 26, °R;
- $K_1$ = a constant which will be updated on-line as laboratory analyses are obtained with a preliminary set value of 21.0504;
- $K_2$ = a constant which will be periodically updated off-line with a preliminary set value of 16,500; and,
- N, J, L and M = exponents which will be periodically updated off line with preliminary set values of
  N = 0.9
  J = 0.3
  L = 0.3 and
  M = −0.5.

It is to be understood that wherever measurements are made with regard to feed, an allowance has been made for the time it takes the feed to reach the first crystallizer 26 from its source.

Two possible modes of operation are provided for the first crystallizer 26. In the first mode, the ratio of air flow rate to the first crystallizer 26 divided by the pX feed rate to the reactor section 24 is set and changes in oxygen uptake are indicated by changes in the oxygen concentration sensed in the vent 34 from the first crystallizer 26 as defined previously.

In the second mode of operation, the oxygen concentration in the vent 34 from the first crystallizer 26 is set and the air flow to the crystallizer 26 is adjusted to maintain this concentration. In this mode of operation, changes in oxygen uptake are indicated by changes in the air flow rate.

The computer system 28 is programmed to operate using either mode chosen.

Since $CO_2$ generation is another variable to be monitored, the $CO_2$ generation per mole of pX fed into the reactor can be determined by:

$$A = \frac{(7.48)(106.168)(0.79)(BC)}{379\, DEF\,(100-C-G)} \quad (3)$$

where:
- A = moles of $CO_2$ generated per mole of pX being fed into the reactor section 24;
- B = air flow rate to the reactor section 24 in units of SCFM/reactor;
- C = concentration of $CO_2$ in the vent 38 from the reactor section 24 in mole percent;
- D = pX concentration (in weight fraction or decimal) in the reactor input feed stream to the reactor section 24;
- E = density of the reactor section 24 feed in pounds per cubic foot coming from an off-line input;
- F = the flow rate of the reactor input feed stream to the reactor in gpm/reactor; and
- G = the concentration of oxygen in the vent from the reactor section 24 in mole percent.

It is to be noted that the above equation can be rearranged to solve for the $CO_2$ concentration in the vent 38 from the reactor section 24 which is the actual controlled variable. In this respect, the rearranged equation to supply the $CO_2$ concentration is:

$$C = \frac{100\cdot G}{1 + \frac{(7.48)(106.168)(0.79)(B)}{379\, ADEF}} \quad (4)$$

Utilizing another equation set forth below, the first priority of the computer system 28 is to maintain the $CO_2$ generation per mole of pX fed into each reactor at a target value calculated as:

$$A = B(C/D)^N (E/F)^M (G/H)^L \exp[K(1/P - 1/Q)] \quad (5)$$

where:
- A = target value for the $CO_2$ generation per mole of pX fed into each reactor in moles $CO_2$/mole pX feed;
- B = previous lined out value for the average $CO_2$ generation per mole of pX fed into the reactors in moles $CO_2$/mole pX feed;
- C = setpoint value for the first crystallizer 26 oxygen uptake per mole of pX fed into reactor section 24 in moles of oxygen/mole of pX feed;
- D = previous lined out value for the first crystallizer 26 oxygen uptake per mole of pX fed into reactor section 24 in moles oxygen/mole of pX feed;
- E = a throughput term obtaind by multiplying the current values of the following three variables together:
  1. the pX concentration (in weight fraction or decimal) in the reactor feed input stream allowing for the time delay between the reactor feed input stream and the first crystallizer;
  2. the density of the reactor feed input stream in pounds per cubic foot, and
  3. the flow rate of the reactor feed input stream in gpm, allowing for the time delay between the reactor feed input stream and the first crystallizer;
- F = a previous, lined-out, value for the throughput term given by "E";
- G = the current atom ratio in the reactor feed input stream in units of moles of bromine per moles of metals;
- H = previous, lined-out atom ratio in the reactor feed input stream;
- P = previous, lined-out average absolute temperature in the reactor section 24 in °R;
- Q = the current average absolute temperature in the reactor section 24 in °R;
- K = a constant which will be periodically updated off-line and which has a preliminary set value of 11800; and
- N, M, L = exponents which will be periodically updated off line with preliminary set values of
  N = −0.25
  M = −0.31 and
  L = 0.12.

With the above calculation, a new target value is constantly being calculated for $CO_2$ generation. Thus, the calculation is updated whenever a lined-out value for the first crystallizer 26 oxygen uptake per mole of pX feed feed in reactor section 24 is outside of the minimum or maximum value allowable, while the $CO_2$ generation per mole of pX feed in the reactor section(s) 24 is lined out at the target value.

It will be noted that the above equation does not take into account the effects of the solvent ratio, the water concentration, or the oxygen partial pressure in the reactor section 24 since the effects of varying these variables or parameters are minor in nature. However, that is not to say that values for these variables or parameters cannot be included in the correlation. It should be remembered that although the water concentration affect on the $CO_2$ generation at a given 4-CBA concentration is minor, the water concentration can be used, as well as the reactor temperature and catalyst concentration, to adjust the content of 4-CBA in the reactor section 24 to control the $CO_2$ generation.

In this respect, water concentration in the reactor section 24 can be adjusted to control the $CO_2$ generation in the reactor section 24 by changing the ratio of the flow rate of water withdrawal (WWD) divided by the feed rate of pX being fed into the reactor section 24. The adjustment of this ratio can be guided by the following correlation:

$$A = B[1 + (CD/EFG)(P + KQ)((R/S)^N)] \quad (6)$$

where:
- A = a setpoint or target value for the ratio of the flow rate of the WWD divided by the feed rate of pX into the reactor stage 24 (gpm WWD/reactor)/(mole pX feed/hr/reactor);
- B = measured value for ratio given in A (should equal previous set point value) (same units as A) (−13.24G/CDQ);
- C = flow rate of the input feed stream to the reactor section 24 in units of gpm/reactor
- D = density of the reactor feed input stream in pounds per cubic foot;
- E = water concentration in WWD (in weight fraction or decimal);
- F = density of WWD in pounds per cubic foot;
- G = measured value for the flow rate of the WWD in gpm/reactor;
- P = water concentration (in weight fraction or decimal) in reactor feed input stream;
- Q = pX concentration (in weight fraction or decimal) in the reactor feed input stream
- R = setpoint or target value for the $CO_2$; generation per mole of pX fed into the reactor, mole $CO_2$/mole pX feed;
- S = measured $CO_2$ generation per mole of pX feed in the reactor, mole $CO_2$/mole pX feed;
- K = a constant which will be periodically updated off-line with a preliminary set value of 0.37;
- N = an exponent which will be periodically updated off-line with a preliminary set value of 6.6.

When required, changes in water concentration in the reactor section 24 can be made most rapidly by maximizing or minimizing the flow rate of the WWD until the target concentration is obtained. However, this is not the preferred method of changing water concentration since rapid, large changes in the flow rate of the WWD can lead to significant changes in the reactor solvent ratio. Therefore, the variation in the WWD flow rate should be made slowly within acceptable limits.

When a target value of $CO_2$ generation per mole of pX feed in the reactor section 24 is at a target value, the reactor section 24 water concentration can be maintained by adjusting the flow rate of the WWD to compensate for changes in flow rate and/or composition of the feed to the reactor section 24. The following equation is utilized to determine appropriate WWD flow rate:

$$A = B + \frac{C[D(E + KF) - G(H + KP)]}{QR} \quad (7)$$

where:
- A = setpoint or target value for the flow rate of WWD, gpm/reactor;
- B = previous flow rate of WWD, gpm/reactor;
- C = density of reactor input feed stream in pounds per cubic foot;
- D = current flow rate of the reactor input feed stream in gpm/reactor;
- E = current water concentration in the reactor feed input stream in weight percent;
- F = current pX concentration in the reactor input feed stream in weight percent;
- G = previous flow rate of the reactor input feed stream in gpm/reactor;
- H = previous water concentration in reactor input feed stream in weight percent;
- P = previous pX concentration in the reactor input feed stream in weight percent;
- Q = density of the WWD in pounds per cubic foot;
- R = water concentration in the WWD in weight percent;
- K = constant which should match K in the last equation (7) above and which is periodically updated off-line but has a preliminary set value of 0.37.

The temperature in each reactor section 24 can also be adjusted to control $CO_2$ generation in the reactor section 24 by changing pressure within the reactor section 24. The adjustment can be guided by the following equation:

$$A = KB/[K + B \ ln(C/D)] \quad (8)$$

where:
- A = setpoint or target value for the absolute reactor temperature °R;
- B = a measured value for the absolute reactor temperature which should equal the previous setpoint or target value in °R;
- ln = natural logarithm;
- C = measured $CO_2$ generation per mole of pX fed into the reactor in moles $CO_2$/mole of pX feed;
- D = setpoint or target value for the $CO_2$ gneration per mole of pX fed into the reactor in moles $CO_2$/mole of pX feed;
- K = a constant which will be periodically updated off line and which has a preliminary set value of 16090.

It is important to be able to adjust the temperature within the reactor section 24 because variations in temperature from a target temperature can lead to offsets.

The catalyst concentration in the reaction section 24 can also be adjusted to control the $CO_2$ generation in the reactor section 24 by changing the setpoint or target value for the catalyst concentration in the reactor input feed stream. The most rapid response can be obtained by maximizing or minimizing catalyst concentration within acceptable limits until the target concentration is reached. However, to prevent oscillating concentration changes, the catalyst concentration in the reactor input feed stream should be set at a value which will result in the target $CO_2$ generation per mole of pX feed in the reactor section 24 at steady state. Then $CO_2$ generation can be monitored until a steady-state value is achieved.

The metal catalyst concentration adjustment in the reactor input feed stream can be calculated by:

$$A = B(C/D)^N \quad (9)$$

where:
- A = setpoint or target value for the catalyst concentration in the reactor input feed stream in weight percent;
- B = measured value for the catalyst concentration in the reactor input feed stream which should equal the previous set point, in weight percent;
- C = setpoint or target value for the $CO_2$ generation per mole of pX fed into the reactor in mole $CO_2$/mole pX feed;
- D = measured carbon dioxide generation per mole of pX feed in the reactor section 24 in units of mole $CO_2$/mole pX feed;
- N = an exponent which will be periodically updated off-line with a preliminary set value of 1.5.

It is to be noted however that since the catalyst concentration in the reactor input feed stream has an affect on all reactor sections 24, it may be necessary to adjust water concentration in the manner explained above and to adjust temperature in the manner explained above in some of the reactors when the catalyst concentration is adjusted in one reactor section 24.

The computer system 28 has also been designed to control a single indicator of optical properties of crude TA at a target or setpoint value. In order to control the optical properties of the crude TA product, the indicator variable for the crude TA must correspond to the quality of purified TA. For this purpose fluorescence of the crude TA leaving the product recovery stage 16 is monitored and utilized as an indicator of optical properties.

The optical properties as measured by fluorescence of the dried cakes of TA output product are maintained at a target value by controlling oxygen concentration in the vent 38 from the reactor section 24. The target value for oxygen concentration is determined as follows:

$$A = \left[ \frac{K_1 B^N C^M (DEF)^L}{G(1 - K_2 H - K_3 P)\exp(K_4/Q)} \right]^J \quad (10)$$

where:
- A = oxygen concentration in the vent 38 from the reactor section 24 in mole percent;
- B = setpoint or target value for 4-CBA in weight percent in the dried cakes of TA product;
- C = atom ratio in the reactor input feed stream in moles bromine per moles metals;
- D = pX concentration (in weight fraction or decimal) in the reactor input feed stream;
- E = density of the reactor input feed stream in pounds per cubic foot;
- F = flow rate of reactor input feed stream in gpm/reactor;
- G = setpoint or target value for the indicator of optical properties, i.e., fluorescence of the "dryer cake";
- H = MLR (Mother Liquor Recycle) effect (see equation 11 below);
- P = CRU (Catalyst Recovery Unit) effect (see equation 12 below);
- Q = absolute temperature in the reactor in °R
- $K_1$ = a constant which will be updated on-line as analyses are obtained with a preliminary set value of 2.29;
- $K_2$, $K_3$ and $K_4$ = constants which will be periodically updated off line with preliminary set values of
  - $K_2$ = 0.88
  - $K_3$ = 0.41
  - $K_4$ = 9000;
- N, M, L, J = exponents which will be periodically updated off-line with preliminary set values of:
  - N = 0.5
  - M = 0.3
  - L = 1.1
  - J = 2.0.

The MLR effect "H" is calculated by:

$$H = (A - B)/C \quad (11)$$

and the CRU effect "P" is calculated by $$P = B/C \quad (12)$$

where:
- A = the flow rate of cobalt in the reactor input feed stream into the feed preparation stage 10 in pounds per hour;
- B = the flow rate of cobalt in the reactor input stream into the reactor stage 12 in pounds per hour;
- C = a 1-hour average for the flow rate of cobalt in reactor input feed stream in pounds per hour.

The average defined as "C"0 above excludes any unusual conditions which may affect flow rate.

Although it would be possible to correlate additional parameters such as solvent ratio and water concentration in the reactor section 24 and the temperature in the crystallizer 26 into the above equation, the effect of adding these variables in would be minimal since they are controlled over a relatively narrow range as described above.

Further, in the equation 10 immediately above, a constant oxygen concentration controls the optical properties, in essence, if the other reactor conditions, the MLR stream and the CRU recycle stream, are adequately controlled.

The overall computer system 28 will control automatically the reactor conditions and the flow rate of the MLR stream per mole of pX feed. However, at times, adjustments may need to be made to the flow rate of the CRU recycle stream per mole of pX feed in order to purge sodium from the stream, to reduce the amount of recycled catalyst, as a result of a possible operating problem in the CRU.

Therefore, changes in the target value of oxygen concentration in the vent 38 from the reactor section 24 can be expected. In the process, once the oxygen concentration is altered to obtain the desired target value for same, the computer system 28 automatically will adjust all other operating variables as required to control the 4-CBA content in the TA output product.

As may occur, however, if the oxygen concentration in the vent 38 from the reactor section 24 is necessarily found to be outside of the allowable range in order to control the optical properties of the output product, the concentration of the oxygen will be set at the limiting value and a signal will be issued by the computer system 28 to the operator to adjust the MLR ratio defined above. It is unlikely, however, that this will be necessary since the entire effect of the CRU recycle, which contributes only 5% of the opticals at an 85% MLR, can be compensated for by a change in the oxygen concentration in the vent 38 from the reactor section 24 of less than 1.5 mole percent.

In an alternative embodiment one may maximize the MLR ratio subject to product quality constraints at any given set of operating conditions.

The oxygen concentration in the vent 38 from the reactor section 24 can be maintained and controlled at the target value given in equation (10) pertaining to oxygen concentration by adjusting the setpoint or target value for the ratio of the flow rate of air to the reactor section 24 divided by the rate of pX feed. The air flow rate is then adjusted if the oxygen concentration in the vent 38 from the reactor section 24 differs from the setpoint or target value by more than a predetermined acceptable variance (such as, for example, 0.1 mole percent). This adjustment can be made by standard control methods or may be estimated by the following material balance equation:

$$A = \frac{B[(21-C)(100-D-E) + D(E-C)]}{(21-E)(100-D-C)} \quad (13)$$

where
- $A$ = required air flow rate in units of SCFM/reactor;
- $B$ = previous air flow rate in units of SCFM/reactor;
- $C$ = previous $O_2$ concentration in the reactor vent in mole percent;
- $D$ = $CO_2$ concentration in the reactor vent in mole percent, and
- $E$ = setpoint or target value of oxygen concentration in the reator vent in mole percent.

The correlations which control the percentage of 4-CBA in dried TA product (equation 2) and the fluorescence index (equation 10), each contain a constant $K_1$ which is updated on-line as laboratory analyses are obtained. The data filtering technique utilized to reassure that realistic values are entered into the computer system 28 are described hereinafter.

The value obtained by the laboratory analyses and the time at which the sample is taken will be entered into the computer system 28. The system 28 will then determine the lined-out operating conditions which existed in the reactor section 24 and the first crystallizer 26 when the material being analyzed was in these vessels (reactor and crystallizer). The time delay between the reactor and the dryer is calculated utilizing vessel inventories and measured flow rates. A new constant $K_1$ for the equation defined above determining setpoint or target value of first crystallizer 26 oxygen uptake per mole of pX feed feed is then calculated using the following equation:

$$K_1 \text{ in the equation (2)} = \quad (14)$$

$$K_2/F + \ln\left(\frac{A}{B^N C^J D^L E^M}\right)$$

where:
- $A$ = first crystallizer 26 oxygen uptake per mole of pX feed to reactor section 24 in mole $O_2$/mole pX feed;
- $B$ = measured value for the 4-CBA in weight percent in the dryer cake;
- $C$ = $O_2$ concentration in the vent from the first crystallizer in mole percent;
- $D$ = concentration of cobalt in the reactor input feed stream in ppm;
- $E$ = a throughput term obtained by multiplying together:
  1. pX concentration (in weight fraction or decimal) in the reactor input stream;
  2. density of the reactor input feed stream in pounds per cubic foot (off-line input);
  3. flow rate of the reactor input feed stream in gpm;
- $F$ = absolute temperature in the first crystallizer in °R;
- $K_2$, $N$, $J$, $L$, $M$ = constant and exponents from equation (2) which are periodically updated off-line but which have preliminary set values of
  - $K_2 = 16500$
  - $N = 0.9$
  - $J = 0.3$
  - $L = 0.3$
  - $M = -0.5$;
- $\ln$ = natural logarithm.

A new constant for use in equation (10) above for determining oxygen concentration is calculated as follows:

$$K_1 \text{ in equation (10)} = \quad (15)$$

$$\frac{A^{1/J}(R - K_2 GH - K_3 GP)\exp(K_4/Q)}{B^N C^M (DEF)^L}$$

where:
- $A$ = $O_2$ concentration in the vent from the reactor in mole percent;
- $B$ = measured value of 4-CBA in weight percent in the dryer cake;
- $C$ = atom ratio in the reactor input feed stream in moles Br/moles metals;
- $D$ = pX concentration (by weight) in the reactor input feed stream in decimal units;
- $E$ = density of the reactor input feed stream in pounds per cubic foot;
- $F$ = flow rate of the reactor input feed stream in gpm/reactor;
- $G$ = setpoint value for indicator of optical properties, i.e., flourescence in this embodiment;
- $H$ = MLR effect (see equation 11);
- $P$ = CRU effect defined above (see equation 12);
- $Q$ = absolute temperature in the reactor in °R;
- $R$ = measured value for the indicator of optical properties, i.e., measured dryer cake fluorescence;
- $K_2$, $K_3$, $K_4$, $N$, $M$, $L$, $J$ = constants and exponents in equation relating to $O_2$ concentration which are periodically updated off-line and which have preliminary set values of
  - $K_2 = 0.88$
  - $K_3 = 0.41$
  - $K_4 = 9000$
  - $N = 0.5$
  - $M = 0.3$
  - $L = 1.1$
  - $J = 2.0$.

The constants $K_1$ obtained from calculations of equations (14 and 15) are compared, respectively, to the previous values for the filtered constants $K_F$. If the value for either $K_1$ differs from $K_F$ by more than 10%, the computer system 28 will call for a repeat analysis.

When a consistent value for $K_1$ is finally obtained, the filtered constant $K_F$ will then be updated using the following equation:

$$K_{FN} = C K_1 + (1-C) K_{FO} \quad (16)$$

where:
- $K_{FN}$ = new filtered constant;
- $K_1$ = new unfiltered constant;
- $C$ = constant limited to values between zero and one from off-line input, and
- $K_{FO}$ = previous filtered constant.

Note that in the above equation, as C decreases, the response will tend to become slow to real changes being made in the process. Alternatively, as C increases, measurement errors will tend to be interpreted as changes in the process. Therefore a preferred primarily set value of 0.5 for C is utilized, which is halfway between the limits placed on the value of C.

Further, it is to be understood that when the new constant $K_1$ for equation (2) or equation (10) is changed, the allowable range for the control variable will be changed. This may result in the value of that control variable being outside of the allowable range for some (constraint limits) even though it has not changed from a value that previously was within the allowable range. This may require adjusting of the other control variables or recalibrating the constraint limits.

Figure 3:
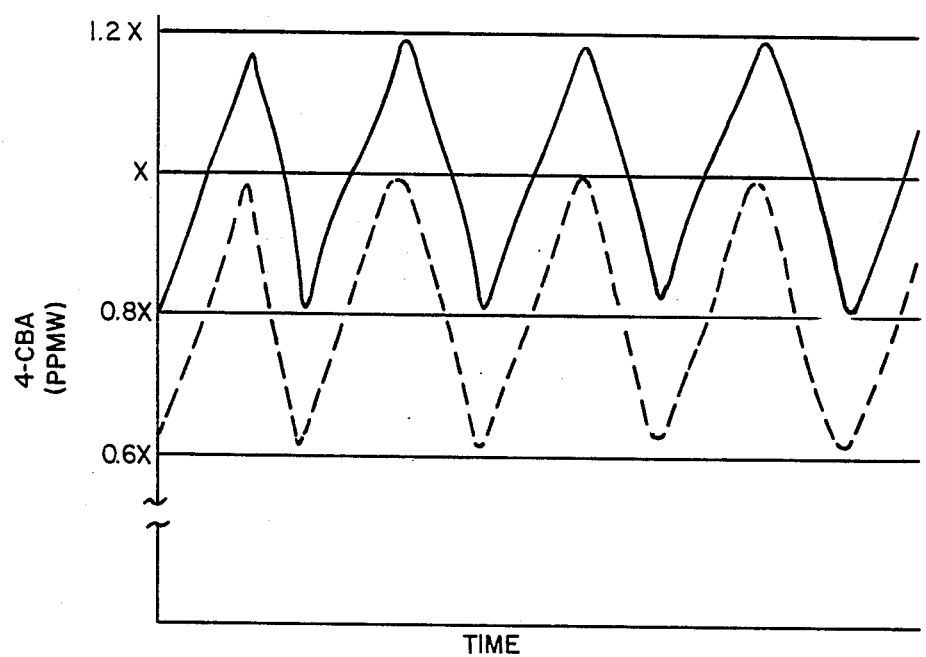
FIG. 3 is a graph of the amount of 4-carboxy-benzaldehyde (4-CBA) found in the conventional manufacture of terephthalic acid and shows the fluctuation of the amount of 4-CBA in the terephthalic acid product as it is produced over a period of time.

Referring now to FIG. 3, there is illustrated therein the typical fluctuation of the 4-CBA in parts per million by weight (ppmw) in the product from a conventional process for manufacturing TA. Here for example, to obtain a TA product having an average of X ppmw of 4-CBA one would typically produce TA output product having between about 0.8 X ppmw and about 1.2 X ppmw of 4-CBA.

This causes problems for a customer since the strength of the polyester made from the TA will vary over a fairly wide range and the customer may really want a product that has no higher than X ppmw of 4-CBA. However, to produce 4-CBA with this upper limit one would have to operate at a lower average production of 4-CBA, typically with an average 4-CBA of about 0.8 X ppmw. Typically what happens is that to compensate for high compositions of 4-CBA the process must be operated to produce a corresponding amount of low composition 4-CBA. This increases the cost of the production of the TA since the higher the operating point in terms of 4-CBA content in the TA, the less the amount of acetic acid solvent required.

Furthermore, if the swing or variance in the concentration of 4-CBA in the TA output product is kept as small as possible a higher quality TA product is produced for customers.

Figure 4:
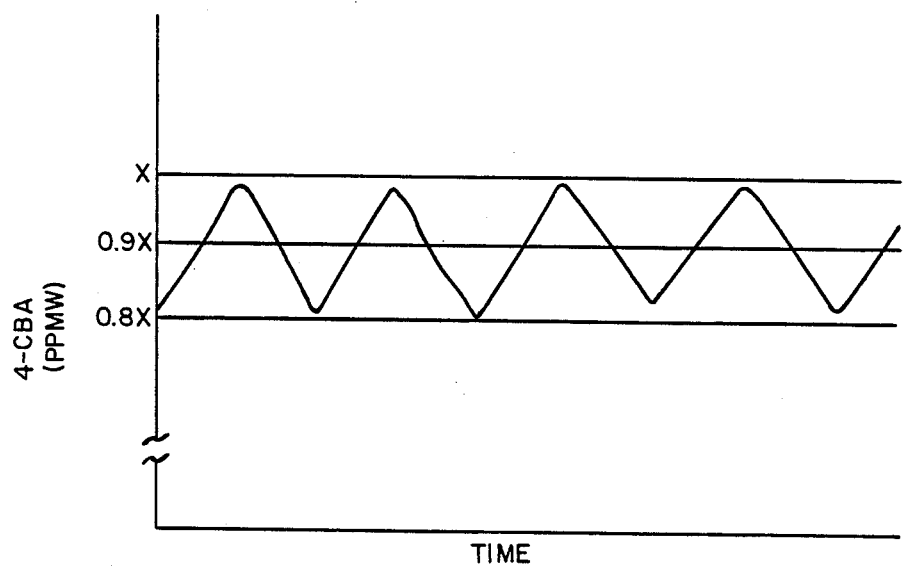
FIG. 4 is a graph of the amount of 4-CBA in a terephthalic acid output product and the fluctuations of the amount of 4-CBA in the terephthalic acid output product as it is being produced over a period of time using the method of the present invention.

It will be appreciated from FIG. 4 that to provide a TA output product having a 4-CBA content of approximately about 0.9 X ppmw one can operate the process of FIG. 1 utilizing the method of the present invention to produce TA output product having a variance or range of 4-CBA content between about 0.8 X ppmw and about X ppmw or less. This provides a better quality control of the output product for customers whereby they can produce polyester elastomers which have a more uniform strength and breakdown characteristics.

Additionally, the process can be operated at a higher level of 4-CBA content which results in a much lower need for acetic acid solvent thereby significantly reducing the cost of operating the process.

Typically with prior art processes, the range in 4-CBA content would be approximately ±20% from the mean value whereas in a process for manufacturing TA output product utilizing the method of the present invention one can obtain a variance in the 4-CBA content of as low as ±4% from the mean value.

From the foregoing description it will be apparent that the method of the present invention and the computer system operated apparatus for carrying out the method of the present invention for manufacturing terephthalic acid (TA) which has a more uniform quality control in terms of 4-CBA content and optical density, has a number of advantages, some of which have been described above and others of which are inherent in the invention.

Also it will be apparent from the foregoing description that modifications can be made to the method of the present invention and the apparatus for implementing same without departing from the teachings of the present invention. Accordingly, the scope of the invention is only to be limited as necessitated by the accompanying claims.

We claim:

1. A method for manufacturing terephthalic acid (TA) having a closely controlled, desired amount of 4-carboxy-benzaldehyde as contaminant therein and in which method a feed of para-xylene mixed with a catalyst comprising soluble forms of cobalt, manganese and bromine and wherein cobalt (calculated as elemental cobalt) can be present in the range of from about 0.1 to about 10.0 milligram atoms (mga) per gram mole of the alkyl aromatic; manganese (calculated as elemental manganese) can be present in a ratio of from about 0.1 to about 10.0 mga per mga of cobalt (calculated as elemental cobalt); and bromine (calculated as elemental bromine) can be present in a ratio of from about 0.2 to about 1.5 mga per mga of the total cobalt and manganese (both calculated as elemental metals), and a solvent system comprising acetic acid is fed to a reactor stage comprising one or more reactors with oxygen for carrying out an exothermic oxidation reaction in the reactor stage, and an output slurry from the reactor stage is fed with oxygen to a first crystallizer of a crystallizing stage, said method comprising the steps of:

determining empirical relationships between (1) the desired level of the 4-carboxy-benzaldehyde contaminant in the TA output product from the crystallizing stage and the oxygen uptake in the first crystallizer and (2) the oxygen uptake in the first crystallizer and the $CO_2$ in the vent gas from the reactor stage;

monitoring the $CO_2$ in the vent gas from the reactor stage;

adjusting operating variables of the reactor stage within minimum and maximum constraints thereof to adjust the reactor vent $CO_2$ to a desired level, wherein said reactor operating variables are: (1) reactor temperature of between 350° F. and 500° F., (2) reactor water content of between 5% and 20% by weight, (3) weight percent of each, and/or the ratio between the catalysts supplied to the reactor(s) and (4) the level of material in the reactor of between 50% and 90% by volume.

2. The method of claim 1 including the step of:
once the desired $CO_2$ level is obtained, confirming that the oxygen uptake in the first crystallizer is the value it should be relative to the $CO_2$ in the reactor vent gas.

3. The method of claim 1 including the step of:
if the oxygen uptake in the crystallizer is not the desired value, obtaining a new target value for the reactor vent $CO_2$ content from the empirically determined relationships.

4. The method of claim 1 including the step of:
(analyzing analytically) the percentage of the contaminant in the dried TA output product to make certain it is within the desired range.

5. The method of claim 1 including the steps of:
determining empirically a mathematical relationship between the oxygen in the vent gas from the reactor stage and opticals or optical density of the TA output product;
monitoring the oxygen in the vent gases;
and adjusting the air intake to the reactor stage until the oxygen in the reactor vent gas is at a desired level in the range of about 1% to about 12%, to provide TA output product with a desired optical density.

6. The method of claim 1 including the step of:

recalibrating and resetting the maximum and minimum limits of the reactor operating variables if after all of them are set to their limits and the reactor vent gas $CO_2$ is still not at a desired level thereof.

7. The method of claim 1 including the step of:
recalibrating the relationship between carbon dioxide in the vent gas from the reactor stage and the oxygen uptake in the first crystallizer, if all of the limits of the reactor operation variability are set to their limits and the reactor vent gas is still not at a desired level thereof.

8. The method of claim 1 including the step of:
resetting the target for the oxygen uptake in the first crystallizer and the target for the carbon dioxide in the vent gas from the reactor stage to get the reset oxygen uptake target and recalibrating the relationship between carbon dioxide in the vent gas from the reactor stage and the oxygen uptake in the first crystallizer if the analyzed concentration of the 4-carboxybenzaldehyde contaminant in the TA output product is not at the previously empirically determined value.

9. The method of claim 1 wherein said operating variables are adjusted between respective range constraint of each variable in the order of variables (1), (2), (3) and (4) until a desired $CO_2$ reactor vent gas content is obtained.

10. The method of claim 5 wherein said reactor vent oxygen is adjusted to be between 1% and 12% by volume of the reactor vent gas to adjust the optical density between 0.5 and 1.5.

11. The method of claim 3 wherein said solvent is acetic acid and said method is operated to produce, dependent upon the customer needs, a TA output product having an amount as high as possible of contaminant, 4-CBA, to have as low as possible consumption of acetic acid solvent in the manufacture of the TA product.

12. The method of claim 1 wherein the first crystallizer oxygen uptake per mole of pX feed to the reactor section is determined by the equation:

$$A = \frac{(7.48)(106.168)(B)[0.21 - 0.79C/(100-C-G)]}{379\ DEF}$$

where:
A = first crystallize oxygen uptake per mole of pX feed to the reactor section in units of moles $O_2$/mole of pX feed;
B = air flow rate to the first crystallizer, in units of SCFM (Standard Cubic Feet per Minute);
C = oxygen concentration in the vent from the first crystallizer in units of mole percent;
D = pX concentration (in weight fraction or decimal) in the reactor feed input stream;
E = density of incoming reactor feed input stream in pounds per cubic foot;
F = flow rate of the incoming reactor feed input stream in gpm (gallons per minute), and
G = carbon dioxide concentration in the vent from the first crystallizer in mole percent.

13. The method of claim 1 wherein a setpoint for the first crystallizer oxygen uptake per mole of paraxylene (pX) feed to the reactor section is determined by using the following correction:

$$A = B^N C^J D^L E^M \exp(K_1 - K_2/F)$$

where:
A = first crystallizer oxygen uptake per mole of pX feed to the reactor section in moles $O_2$ oxygen/mole of feed;
B = setpoint or desired value for the 4-CBA in weight percent;
C = oxygen concentration in the vent from the first crystallizer in mole percent;
D = concentration of cobalt in the reactor feed input stream in ppm allowing for the time delay between the reactor feed input stream and the first crystallizer;
E = a throughput term obtained by multiplying together:
 1. the pX concentration (in weight fraction or decimal) in the reactor feed input stream allowing for the time delay between the reactor feed input stream and the first crystallizer;
 2. the density of the reactor feed input stream in pounds per cubic foot, and
 3. the flow rate of the reactor feed input stream in gpm, allowing for the time delay between the reactor feed input stream and the first crystallizer;
F = the absolute temperature in the first crystallizer, °R;
$K_1$ = a constant which will be updated on-line as laboratory analyses are obtained with a preliminary set value of 21.0504;
$K_2$ = a constant which will be periodically updated off-line with a preliminary set value of 16,500; and,
N, J, L and M = exponents which will be periodically updated off line with preliminary set values of
N = 0.9
J = 0.3
L = 0.3 and
M = −0.5.

14. The method of claim 1 wherein said method maintains the $CO_2$ generation in each reactor at a target value calculated as follows:

$$A = B(C/D)^N (E/F)^M (G/H)^L \exp[K(1/P - 1/Q)]$$

where:
A = target value for the $CO_2$ generation per mole of pX fed into each reactor in moles $CO_2$/mole pX feed;
B = previous lined out value for the average $CO_2$ generation per mole of pX fed into the reactors in moles $CO_2$/mole pX feed;
C = setpoint value for the first crystallizer oxygen uptake per mole of pX feed into the reactor section in moles of oxygen/mole of pX feed;
D = previous lined out value for the first crystallizer oxygen uptake per mole of pX feed into the reactor section in moles oxygen/mole of pX feed;
E = a throughput term obtained by multiplying the current values of the following three variables together:
 1. the pX concentration (in weight fraction or decimal) in the reactor feed input stream allowing for the time delay between the reactor feed input stream and the first crystallizer;
 2. the density of the reactor feed input stream in pounds per cubic foot, and
 3. the flow rate of the reactor feed input stream in gpm, allowing for the time delay between the reactor feed input stream and the first crystallizer;

F = a previous, now updated, value for the throughput term given by "E";

G = the current atom ratio in the reactor feed input stream in units of moles of bromine per moles of metals;

H = previous, lined-out atom ratio in the reactor feed input stream;

P = previous, lined-out average absolute temperature in the reactor section in °R;

Q = the current average absolute temeperature in the reactor section in °R;

K = a constant which will be periodically updated off-line and which has a preliminary set value of 11800; and N, M, L = exponents which will be periodically updated off line with preliminary set values of
N = −0.25
M = 0.31 and
L = 0.12.

15. The method of claim 1 wherein the metal catalyst concentration adjustment in an input feed stream to the reactor(s) is calculated with the following equation:

$$A = B(C/D)^N$$

where:

A = setpoint or target value for the catalyst concentration in the reactor input feed stream in weight percent;

B = measured value for the catalyst concentration in the reactor input feed stream which should equal the previous set point, in weight percent;

C = setpoint or target value for the $CO_2$ generation per mole of pX fed into the reactor in mole $CO_2$/mole pX feed;

D = measured carbon dioxide generation per mole of pX feed in the reactor section in units of mole $CO_2$/mole pX feed;

N = an exponent which will be periodically updated off-line with a preliminary set value of 1.5.

16. The method of claim 5 wherein the target value for reactor vent oxygen for a desired optical density is determined with the following equation:

$$A = \left[ \frac{K_1 B^N C^M (DEF)^L}{G(1 - K_2 H - K_3 P) \exp(K_4/Q)} \right]^J$$

where:

A = oxygen concentration in the vent from the reactor section in mole percent;

B = setpoint or target value for 4-CBA in weight percent in the dried cakes of TA product;

C = atom ratio in the reactor input feed stream in moles bromine per moles metals;

D = pX concentration (in weight fraction or decimal) in the reactor input feed stream;

E = density of the reactor input feed stream in pounds per cubic foot;

F = flow rate of reactor input feed stream in gpm/reactor;

G = setpoint or target value for the indicator of optical properties, i.e., fluorescence of the "dryer cake";

H = MLR (Mother Liquor Recycle) effect;

P = CRU (Catalyst Recovery Unit) effect;

Q = absolute temperature in the reactor in °R;

$K_1$ = a constant which will be updated on-line as analyses are obtained with a preliminary set value of 2.29;

$K_2$, $K_3$ and $K_4$ = constants which will be perodically updated off line with preliminary set values of
$K_2$ = 0.88
$K_3$ = 0.41
$K_4$ = 9000;

N, M, L, J = exponents which will be periodically updated off-line with preliminary set values of:
N = 0.5
M = 0.3
L = 1.1
J = 2.0;

the MLR effect "H" is calculated by:

$$H = (A - B)/C$$

and the CRU effect "P" is calculated by $$P = B/C$$

where:

A = the flow rate of cobalt in the reactor input feed stream into the feed preparation stage in pounds per hour;

B = the flow rate of cobalt in the reactor input stream into the reactor stage in pounds per hour;

C = a 1-hour average for the flow rate of cobalt in reactor input feed stream in pounds per hour.

* * * * *

UNITED STATES PATENT OFFICE
CERTIFICATE OF CORRECTION

Patent No. 4,835,307               Dated May 30, 1989

Inventor(s) Lindhal et al.

It is certified that error appears in the above-identified patent and that said Letters Patent is hereby corrected as shown below:

| Col. | Line | |
|------|------|---|
| 1 | 52 | "$CO_x$" should read --$CO_X$-- |
| 1 | 66 | "continous" should read --continuous-- |
| 2 | 33 | "terephathalic" should read --terephthalic-- |
| 8 | 16 | "PX" should read --pX-- |
| 11 | 23 | "$CO_2$; generation" should read --$CO_2$ generation-- |
| 14 | 10 | "as "C"O" should read --as "C"-- |
| 18 | 54 | "(analyzing analytically)" should read --analyzing analytically-- |
| 19 | 48 | "crystallize" should read --crystallizer-- |
| 21 | 15 | "temeperature" should read --temperature-- |
| 21 | 24 | "0.31" should read -- -0.31-- |

Signed and Sealed this

Twentieth Day of February, 1990

Attest:

JEFFREY M. SAMUELS

*Attesting Officer*     *Acting Commissioner of Patents and Trademarks*